United States Patent
Chen et al.

(10) Patent No.: US 10,076,508 B2
(45) Date of Patent: Sep. 18, 2018

(54) PHARMACEUTICAL COMPOSITIONS FOR INHIBITING ANTIBIOTIC-RESISTANT MICROORGANISMS AND USES THEREOF

(71) Applicant: Peptide Cham Biotech Co., Ltd., Kaohsiung (TW)

(72) Inventors: Chiu-Hung Chen, Kaohsiung (TW); Yeh Chen, Kaohsiung (TW)

(73) Assignee: Peptide Cham Biotech Co., Ltd., Kaohsiung (TW)

( * ) Notice: Subject to any disclaimer, the term of this patent is extended or adjusted under 35 U.S.C. 154(b) by 0 days.

(21) Appl. No.: 15/227,864

(22) Filed: Aug. 3, 2016

(65) Prior Publication Data

US 2017/0035723 A1    Feb. 9, 2017

Related U.S. Application Data

(60) Provisional application No. 62/200,516, filed on Aug. 3, 2015.

(51) Int. Cl.
*A61K 31/27* (2006.01)

(52) U.S. Cl.
CPC .................................. *A61K 31/27* (2013.01)

(58) Field of Classification Search
None
See application file for complete search history.

(56) References Cited

PUBLICATIONS

Aksoy et al (Clin Microbiol Infect 14:411-420, 2008).*
Rivera et al (Mayo Clin Proc 86:1230-1242, 2011).*

\* cited by examiner

*Primary Examiner* — Craig D Ricci
(74) *Attorney, Agent, or Firm* — Liang Legal Group, PLLC

(57) ABSTRACT

This invention provides an antibiotic drug for inhibiting drug-resistant microorganisms. The antibiotic drug comprises Fmoc-Ala-OPfp, and not only has non-cytotoxic for normal human cell but also can inhibit drug-resistant microorganisms.

3 Claims, 3 Drawing Sheets

PHARMACEUTICAL COMPOSITIONS FOR INHIBITING ANTIBIOTIC-RESISTANT MICROORGANISMS AND USES THEREOF

CROSS-REFERENCE TO RELATED APPLICATIONS

This claims the benefits of U.S. Provisional Application No. 62/200,516, filed on Aug. 3, 2015, the disclosure of which is incorporated by reference in its entirety.

FIELD OF THE INVENTION

The present invention provides a pharmaceutical composition for inhibiting antibiotic-resistant microorganisms and uses thereof.

BACKGROUND OF THE INVENTION

Drug resistance means the decreased efficacy of the drug treatment on disease or symptoms. When the drug concentration is not efficient to kill or inhibit the pathogens, the residual pathogens may have resistance to this kind of drug. For example, the bacteria may have drug resistance because antibiotics generated reactive oxygen and then induced DNA mutations.

The mechanism of antibiotics drug resistance is basically controlled by genes; these genes are collectively referred to as drug resistance gene. With respect to these resistance genes, some bacteria are born to have these genes, some may be obtained from other bacteria through the plasmid or transposons. Antibiotics will kill the bacteria under natural environment, but the bacteria with drug resistant genes won't be killed. That means, there will be more and more bacteria with drug resistant genes in the antibiotic environment. Therefore, the more use of antibiotics, the higher proportion of antibiotic-resistant bacteria will be.

Recently, the strong drug resistance bacteria were generated more and more. This phenomenon is because the lack of effective drug to treatment for drug resistant bacteria and excessive abuse of the antibiotics, which results in more than 40,000 deaths each year in Europe and North America. Thus, all the countries are developing new antibiotics to kill the "superbugs" resistant bacteria.

Ampicillin is used as a first-line antibiotic, in clinical, which is commonly used in medical institutes and livestock industry, and thus result in the abuse of antibiotics to induce the antibiotic resistance.

The outpatients of the *E. coli* present 71% drug resistance to ampicillin in Taiwan, and 39.3% in United States. This situation is not only for the first-line antibiotics, but also for most antibiotics. For example, Vancomycin was used only after all other ineffective antibiotics had been treated, which is also been abused recently and generating drug resistant bacteria, such as Vancomycin-Resistant Enterococcus (VRE).

However, the pharmaceutical companies aim on saving costs on research and development, thus using easy method on developing drugs, such as simply modifying the structure of drug compound. For example, replacing the functional group of compound. After using for a time period, the bacteria would generate antibiotic resistance to the modified drugs easily. That is, if there is no new antibiotics been developed, there will be no any effective drug for treating bacteria so as to induce severe bacterial infection and the patient will be incurable.

SUMMARY OF THE INVENTION

To solve the problem, the present invention provides a pharmaceutical composition for inhibiting microorganism, wherein the pharmaceutical composition is a Fmoc-Ala-OPfp.

N-(9-fluorenylmethoxycarbonyl)-L-alanine pentafluorophenyl (Fmoc-Ala-OPfp, CAS: 86060-86-8) is an alanine (Ala) derivative shown as formula I:

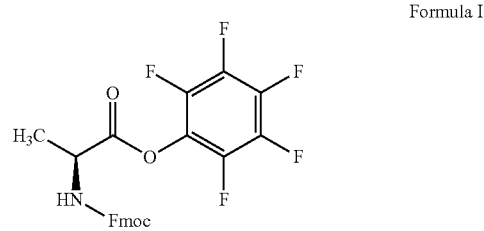

Formula I

Preferably, the microorganism is an antibiotic-resistant microorganism.

Preferably, the antibiotic-resistant microorganism is selected form the group of Gram Positive, *Staphylococcus aureus*, *Staphylococcus epidermidis*, *Streptococcus Pneumoniae*, *Enterococci*, *Clostridium tetani* and *Clostridium botulinum*.

Preferably, the antibiotic-resistant microorganism is *Staphylococcus aureus*.

Preferably, the effective concentration of N-(9-fluorenylmethoxycarbonyl)-L-alanine pentafluorophenyl is 2.5-100 µM.

Preferably, the effective concentration of N-(9-fluorenylmethoxycarbonyl)-L-alanine pentafluorophenyl is 2.5 µM.

Preferably, the antibiotic-resistance is Vancomycin tolerance.

The present invention further provides a method for preparation of the pharmaceutical compositions for inhibiting microorganism, wherein the pharmaceutical compositions comprise Fmoc-Ala-OPfp.

DETAILED DESCRIPTION OF THE INVENTION

Example 1. Antibiotics Activity Test

Figure 3:
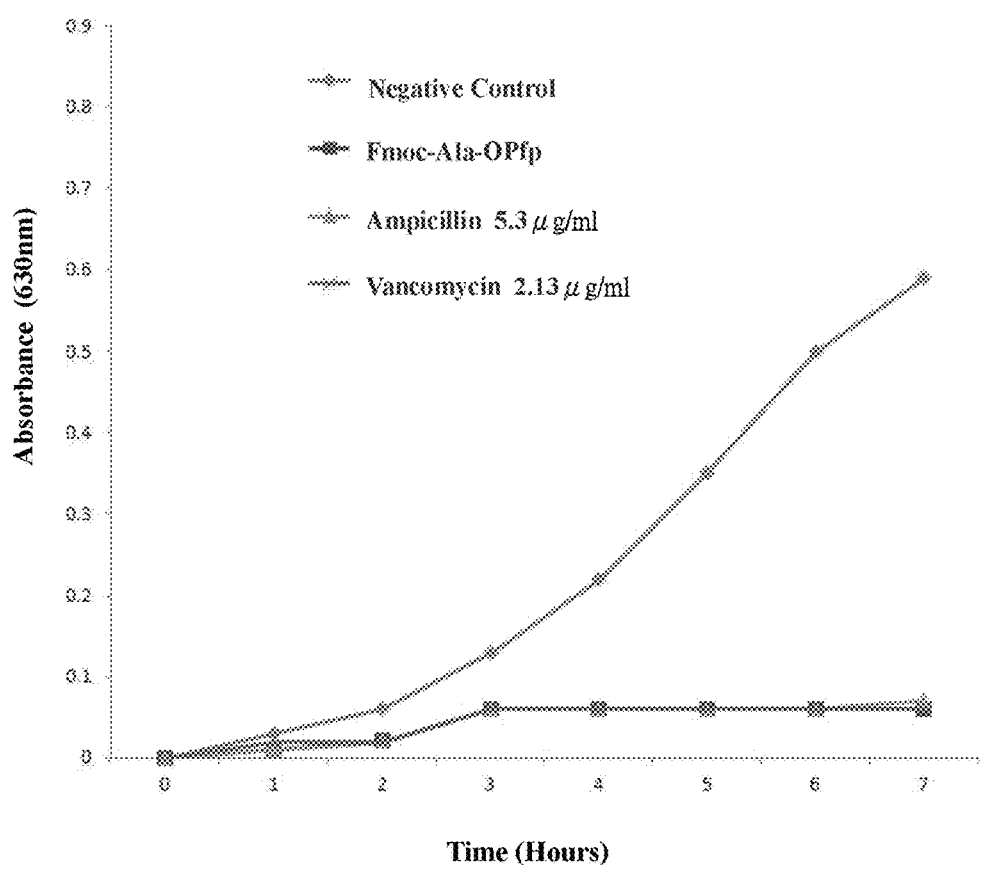
FIG. 3 shows the antibiotic-resistant effects of Fmoc-Ala-OPfp and broad-spectrum antibiotics Ampicillin and Vancomycin on *Staphylococcus aureus*.

The bacteria were cultured for antibiotics activity test. (FIG. 3) The cultured cells were added with specific concentration of Fmoc-Ala-OPfp, Ampicillin and Vancomycin as experimental group, and the cultured cells were not added with any drugs as control group, and the same amount of *Staphylococcus aureus* colonies were added then cultured in an incubator under 37° C. The different time of bacteria concentrations (OD630) were tested to investigate the antibiotic inhibitory effect of Fmoc-Ala-OPfp, Ampicillin and Vancomycin.

Only a small amount (1 μg/ml) of Fmoc-Ala-OPfp was added in the culture medium. Even after the bacterial inoculation for 8 hours, the antibiotic effect was equivalent to 5.3 μg/ml of ampicillin and 5.3 μg/ml vancomycin, which represented Fmoc-Ala-OPfp could effectively inhibit the bacteria growth.

Example 2. Hemolytic Test

Fresh human red blood cells were washed by 0.9% physiological saline for three times, then were dissolved into 2% (V/V) physiological saline, and 50 μL red blood cells suspension and 50 μL of the compound (10, 50 and 100 μg/ml of antibiotic Fmoc-Ala-OPfp) and Triton X-100 was added into the 96-well tray, wherein the final concentration of red blood cells was 2% (V/V). The sample was slightly shaking in the incubator under 37° C. for 1 hour and centrifuged with 2000 g for 30 minutes. 50 μL sample suspension was dropped into a new 96-well tray and the O.D. 490 nm absorbance was measured. The physiological saline and Triton X-100 was negative control group and positive control group, respectively.

Example 3. Cell Culture

Mammalian cell line L292 and MEF cell lines were cultured in Dulbecco's modified Eagle culture medium, wherein the culture medium was added with 100 μg/mL streptomycin, 100 U/mL penicillin and 10% (v/v) fetal bovine serum, and then the cell lines were cultured the in 5% $CO_2$ containing humidified incubator under 37° C.

Example 4. Survival Analysis

MTT assay was used for investigating the cytotoxicity of compound on mammalian cells. The cells were cultured at 96-well tray with 100 μL culture medium for 24 hours after sterilization, then the cells were cultured in the diluted culture medium for 24 hours. 3-(4,5-dimethylthiazol-2yl)-2,5-diphenyltetrazolium bromide (MTT) was added into each well of 96-well tray and incubated for 4 hours. The cell suspension was removed and 100 μL dimethyl sulfoxide was added for dissolving all the precipitate. Enzyme immunoassay instrument was used for measure the 570 nm absorbance.

Figure 1:
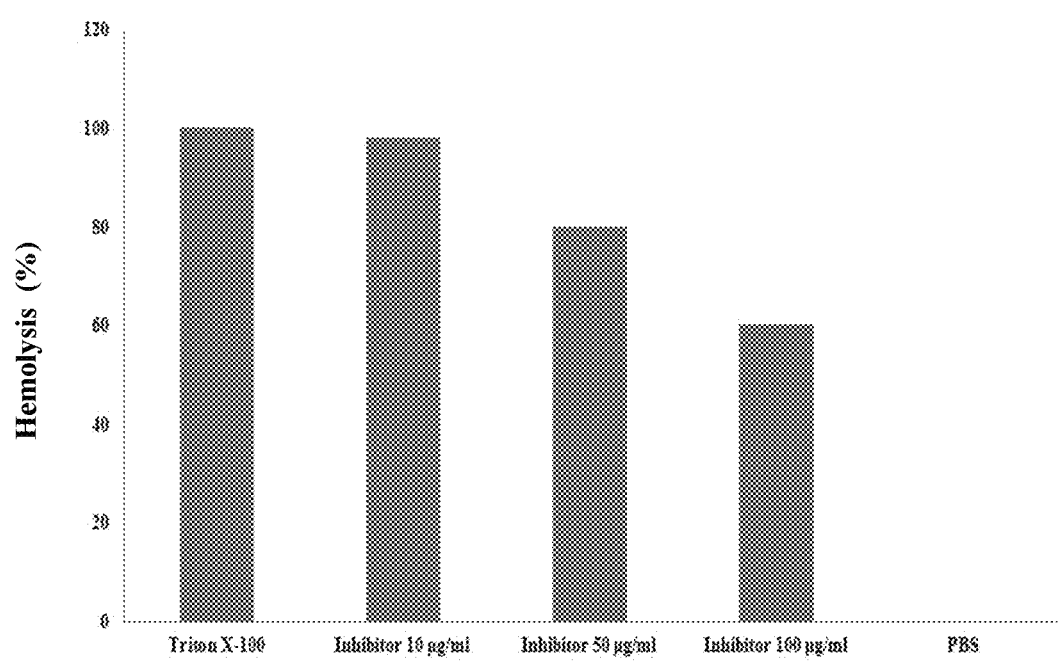
FIG. 1 shows the result of hemolysis test of Fmoc-Ala-OPfp.
Figure 2:
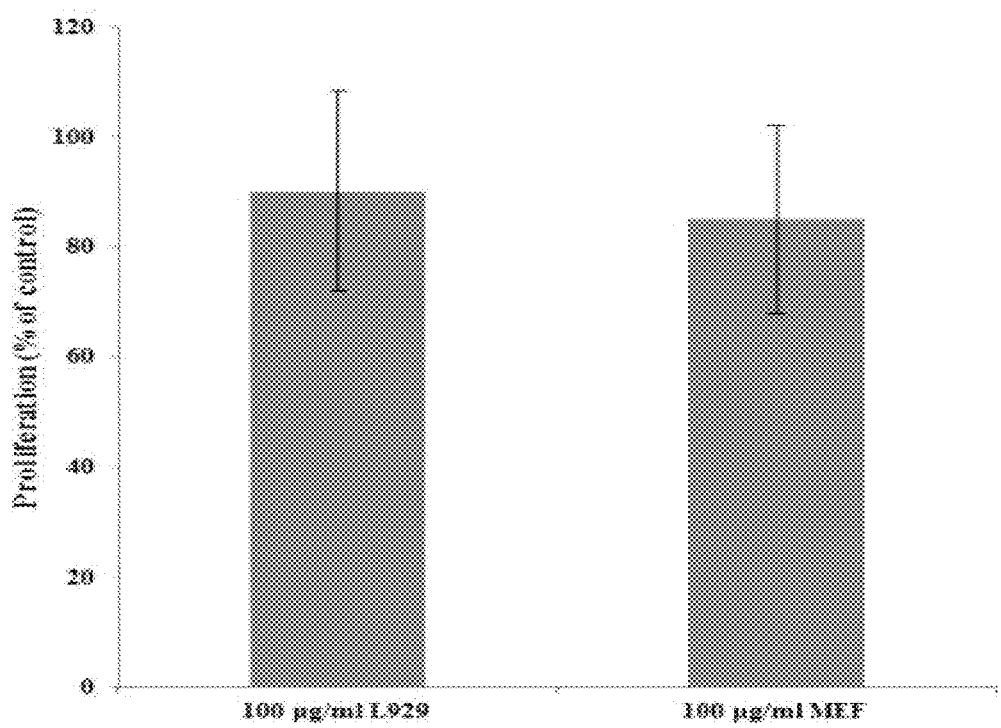
FIG. 2 shows the result of cytotoxicity test of Fmoc-Ala-OPfp on human cells.

The hemolytic test result of human red blood cells and Fmoc-Ala-OPfp MTT assay test results were shown in FIG. 1 and FIG. 2. Fmoc-Ala-OPfp still showed low hemolytic activity at 100 m/mL at concentrations, and the 100 μg/mL of Fmoc-Ala-OPfp only showed 10-20% cell toxicity on MTT assay.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

What is claimed is:

1. A method for inhibiting *Staphylococcus aureus*, comprising contacting N-(9-fluorenylmethoxycarbonyl)-L-alanine pentafluorophenyl (Fmoc-Ala-OPfp) with *Staphylococcus aureus*, wherein N-(9-fluorenylmethoxycarbonyl)-L-alanine pentafluorophenyl has a structure shown as formula I:

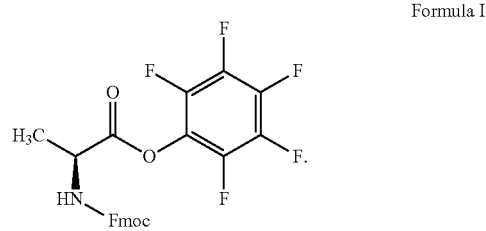

Formula I

2. The method of claim 1, wherein an effective concentration of N-(9-fluorenylmethoxycarbonyl)-L-alanine pentafluorophenyl is 2.5-100 μM.

3. The method of claim 1, wherein an effective concentration of N-(9-fluorenylmethoxycarbonyl)-L-alanine pentafluorophenyl is 2.5 μM.

* * * * *